(12) United States Patent
Rossen et al.

(10) Patent No.: US 6,512,127 B2
(45) Date of Patent: Jan. 28, 2003

(54) PROCESS FOR THE PREPARATION OF HYDROXYLACTONES

(75) Inventors: Kai Rossen, Hanau (DE); Stefan Eils, Hanau (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/935,770

(22) Filed: Aug. 24, 2001

(65) Prior Publication Data

US 2002/0038040 A1 Mar. 28, 2002

(30) Foreign Application Priority Data

Aug. 30, 2000 (DE) .......................... 100 42 643

(51) Int. Cl.⁷ .................. C07D 307/26; C07D 307/02
(52) U.S. Cl. .......................... 549/323; 549/295
(58) Field of Search .................. 549/323, 295

(56) References Cited

FOREIGN PATENT DOCUMENTS

| DE | 198 43 875 | 3/2000 |
|---|---|---|
| DE | 199 13 396 | 9/2000 |

OTHER PUBLICATIONS

Liu et al., "The conversion of racemic terminal opoxides in to either (+) or (–) —doil γ–and δ–lactones", Perkin 1, 2000, vol. 20, pp. 3519–3521, XP001025983.

Tanaka et al., "A simple and practical procedure for the conversion of (S)–4–hydroxymethyl–4–butanolide–4–butanolide into its (R)–enantiomer", Heterocycles, vol. 23, No. 9, 1985, pp. 2347–2350, XP001018770.

Takeichi et al., ""Asymmetric selective polymerzation of –butyrolactone catalyzed by optically active cobalt complex/triethylaluminum system, Polymer Journal, vol. 20, No. 2, 1988, pp. 159–162, XP000000303.

Jacobsen et al., "Polymer–supported chiral Co(Salen) complexes", A. Am. Chem. Soc. vol. 121, No. 17, 1999, pp. 4147–4154, XP001019176.

English language abstract of GR above.

English language abstract of HR above.

*Primary Examiner*—Alan L. Rotman
*Assistant Examiner*—Raymond Covington
(74) *Attorney, Agent, or Firm*—Pillsbury Winthrop LLP

(57) ABSTRACT

The present invention is directed towards a process for the preparation of enantiomerically enriched 4-hydroxymethyl-γ-butyrolactone (I). By kinetic racemate cleavage of racemic epoxide of the general formula (II)

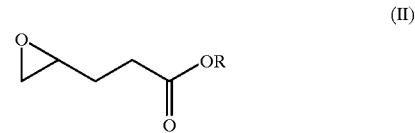

(II)

wherein R represents a $(C_1-C_8)$-alkyl radical, a $(C_8-C_{16})$-aryl radical, with a nucleophile and a Jacobsen catalyst there is obtained enantiomerically enriched (I).

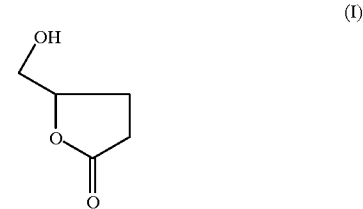

(I)

Use of the lactone so prepared.

14 Claims, No Drawings

PROCESS FOR THE PREPARATION OF HYDROXYLACTONES

The present invention is directed towards a process for the preparation of 4-hydroxymethyl-γ-butyrolactone (I)

(I)

and towards the use thereof.

Enantiomerically enriched (I) is an important intermediate for the preparation of medicaments, it is used especially for the preparation of particular enzyme inhibitors (Synth. Commun. 2000, 30, 1955f.; EP617968). From those specifications, methods of preparing the medicaments starting from (I) and the synthesis of (I) are also described.

The object of the present invention is to provide a further process for the preparation of enantiomerically enriched (I). In particular, that process is to be readily usable on a large scale and is to be superior to the processes of the prior art from an ecological and an economic point of view.

Those objects are achieved by a process having the features of claim 1. Claims 2 to 9 are directed towards preferred embodiments of the process according to the invention. Claim 10 protects a particular use.

By reacting racemic epoxide of the general formula (II)

(II)

wherein R represents a $(C_1-C_8)$-alkyl radical, a $(C_8-C_{16})$-aryl radical, by kinetic racemate cleavage with a nucleophile and a catalyst that contains as the reaction center a tetradentate enantiomerically enriched metal-salene complex, and then carrying out the conversion to (I), there is obtained a process which ensures the preparation of (I) on an industrial scale in high yields and with high enantiomeric excesses.

There is preferably used in the racemate cleavage a catalyst that contains an enantiomerically enriched complex of the general formula (III)

(III)

wherein

M=Cr, Co,

A represents a counter-ion or nucleophile, $R^1$, $R^2$, $R^{1'}$, $R^{2'}$ each independently of the others represents H, $(C_1-C_8)$-alkyl, $(C_1-C_8)$-alkoxy, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, wherein at least one of the radicals may not be H, or $R^1$ and $R^{1'}$ are bonded via a $(C_3-C_5)$-bridge that may be mono- or poly-substituted by $(C_1-C_8)$-alkyl, $(C_1-C_8)$-acyl, $(C_1-C_8)$-alkoxy, $(C_2-C_8)$-alkoxyalkyl and/or may contain hetero atoms such as N, O, P, S in the ring, $R^3$, $R^8$ each independently of the other represents H, $(C_1-C_8)$-alkyl, $(C_1-C_8)$-alkoxy, $(C_6-C_{18})$-aryl, $R^4$, $R^5$, $R^6$, $R^7$ each independently of the others represents H, $(C_1-C_8)$-alkyl, $(C_1-C_8)$-alkoxy, $(C_2-C_8)$-alkoxyalkyl, $(C_1-C_8)$-acyloxy, $(C_1-C_8)$-acyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, or $R^4$ and $R^5$ and/or $R^6$ and $R^7$ are bonded via a $(C_3-C_5)$-bridge that may contain one or more double bonds and/or may be mono- or poly-substituted by $(C_1-C_8)$-alkyl, $(C_1-C_8)$-acyl, $(C_1-C_8)$-alkoxy, $(C_2-C_8)$-alkoxyalkyl and/or may contain hetero atoms such as N, O, P, S in the ring. Most particularly preferred is a catalyst that contains an enantiomerically enriched complex of the general formula (IV)

wherein (IV)

m=from 0 to 4,

M=Cr, Co,

A=Cl, $BF_4$, $SbF_6$, $(C_1-C_8)$-acyl, OH, $H_2O$, $OC(CF_3)_3$, $O(C_6-C_{18})$-aryl, and $R^9$=$(C_1-C_8)$-alkyl, $(C_6-C_{18})$-aryl.

The kinetic racemate cleavage may in principle be carried out without a solvent or in any organic solvent that is inert towards the reaction in question, such as, for example, an ether, especially THF, MTBE.

The temperatures during the racemate cleavage may be from −40° to 50° C., preferably from −20° to +30° C., particularly preferably from −5° to +10° C.

There may in principle be used as the nucleophile any compound that comes into consideration for that purpose to the person skilled in the art. The use of water for that purpose in the kinetic racemate cleavage is, however, most particularly preferred.

When water is used as the nucleophile, there is ideally obtained from the kinetic racemate cleavage by the process according to the invention 0.5 eq. of an enantiomerically enriched diol of the general formula (V)

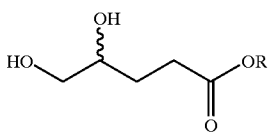

(V)

and 0.5 eq. of the unreacted epoxide (II)

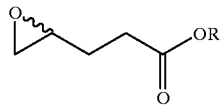

(II)

wherein R in each case may be as defined above.

Under the indicated conditions, (V) immediately cyclises in situ to form the desired enantiomerically enriched lactone (I).

It is, however, within the scope of the invention to separate the two compounds obtainable in the kinetic racemate cleavage and to convert the unreacted enantiomerically enriched epoxide of the general formula (II)

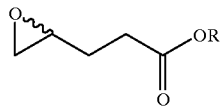

(II)

with acid catalysis, especially with acids such as TFA, $HClO_4$, $H_2SO_4$, $H_3PO_4$ or polymerically bonded acids, to enantiomerically enriched 4-hydroxymethyl-γ-butyrolactone (I). It is also possible to initiate that cyclisation by basic ester cleavage.

Since that reaction yields the same optical enantiomer of (I) as the cyclisation of the diol (V) (Davies et al. Synthesis, 1983, 462), very special preference is given to a process in which the transesterification of the enantiomerically enriched diol (V) and the acid catalysed cyclisation of the enantiomerically enriched epoxide (II) are carried out together in one reaction container.

The scheme below illustrates the possible procedures.

Scheme

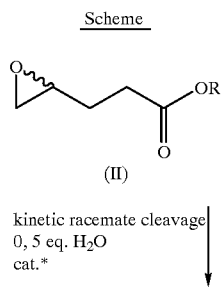

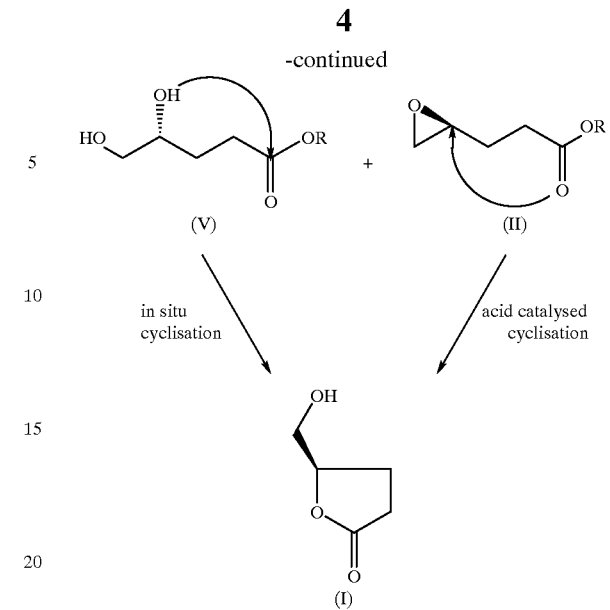

Of course, the enantiomeric series is rendered accessible by use of the enantiomeric catalyst.

In a further embodiment, the invention is directed towards the use of the 4-hydroxymethyl-γ-butyrolactone (I) prepared by the process according to the invention in the preparation of substances having biological activity, especially pharmaceuticals.

The preparation of the racemic starting material is known in the literature (Tetrahedron 1984, 40, 2781–2788; Helv. Chim Acta 1979, 62, 135–139; Indian J. Chem. 1985, 24, 1085–1087).

The present reaction may be carried out using catalysts whose molecular weight has been increased by bonding to a polymer. That bonding may in principle be carried out in a manner known to the person skilled in the art. The bonding is advantageously carried out via one of the substituents $R^4$ to $R^7$ in (III) or $R^9$ in (IV), but it may also be attached at a different position in the molecule. That is dependent on the effect which the bonding to the polymer has on the enantioselective reaction, which can be determined in routine experiments. The compounds according to the invention to be bonded are advantageously coupled to a suitable polymer via a linker, in order to eliminate any disadvantageous interactions between the polymer and the complex (III) or (IV) that may affect the catalytic reaction. With regard to possible linkers, the nature and manner of the bonding to the polymer, and the complex, as well as with regard to suitable polymers, reference is made to specifications DE 100 296 01, DE 100 031 10, DE 100 029 73 and DE 100 029 76 as well as JACS 1999, 121, 4147f. When its molecular weight has been increased in that manner, the homogeneously soluble or heterogenised complex (III) or (IV) may be used particularly advantageously in a membrane reactor, giving rise to the possibility of a quasi-continuous or continuous catalytic reaction (DE 199 10 691.6; Wandrey et al., Tetrahedron Asymmetry 1999, 10, 923–928). That is particularly advantageous on an industrial scale from the point of view of cost.

Within the scope of the invention, enantiomerically enriched denotes the presence of an optical antipode in admixture with the others in an amount >50 mol. %.

($C_1$–$C_8$)-Alkyl radicals are to be regarded as being methyl, ethyl, n-propyl, isopropyl, n-butyl, isobutyl, sec-butyl, tert-butyl, pentyl, hexyl, heptyl or octyl, including all their isomers formed due to different positions of the double bond. The radical $(C_1–C_8)$-alkoxy corresponds to the radical $(C_1–C_8)$-alkyl with the proviso that it is bonded to the molecule via an oxygen atom. $(C_2–C_8)$-Alkoxyalkyl denotes radicals in which the alkyl chain is interrupted by at least one oxygen function, wherein two oxygen atoms may not be bonded together. The number of carbon atoms indicates the total number of carbon atoms contained in the radical.

The radicals just described may be mono- or poly-substituted by halogens and/or by radicals containing N, O, P, S, Si atoms. They are in particular alkyl radicals of the type mentioned above that contain one or more of those hetero atoms in their chain or that are bonded to the molecule via one of those hetero atoms.

$(C_3–C_8)$-Cycloalkyl is to be understood as meaning cyclopropyl, cyclobutyl, cyclopentyl, cyclohexyl or cycloheptyl radicals etc.. They may be substituted by one or more halogens and/or radicals containing N, O, P, S, Si atoms and/or may contain N, O, P, S atoms in the ring, such as, for example, 1-, 2-, 3-, 4-piperidyl, 1-, 2-, 3-pyrrolidinyl, 2-, 3-tetrahydrofuryl, 2-, 3-, 4-morpholinyl.

A $(C_3–C_8)$-cycloalkyl-$(C_1–C_8)$-alkyl radical denotes a cycloalkyl radical as described above that is bonded to the molecule via an alkyl radical as indicated above.

Within the scope of the invention, $(C_1–C_8)$-acyloxy denotes an alkyl radical as defined above that has not more than 8 carbon atoms and is bonded to the molecule via a COO function.

Within the scope of the invention, $(C_1–C_8)$-acyl denotes an alkyl radical as defined above that has not more than 8 carbon atoms and is bonded to the molecule via a CO function.

A $(C_6–C_{18})$-aryl radical is to be understood as being an aromatic radical having from 6 to 18 carbon atoms. Such radicals include especially compounds such as phenyl, naphthyl, anthryl, phenanthryl, biphenyl radicals, which may optionally be substituted by $(C_1–C_8)$-alkoxy, $NR^6R^7$, $(C_1–C_8)$-acyl, $(C_1–C_8)$-acyloxy.

A $(C_7–C_{19})$-aralkyl radical is a $(C_6–C_{18})$-aryl radical bonded to the molecule via a $(C_1–C_8)$-alkyl radical.

A $(C_3–C_{18})$-heteroaryl radical denotes within the scope of the invention a five-, six- or seven-membered aromatic ring system of from 3 to 18 carbon atoms that contains hetero atoms such as, for example, nitrogen, oxygen or sulfur in the ring. Such heteroaromatic compounds are regarded as being especially radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl.

A $(C_4–C_{19})$-heteroaralkyl is to be understood as being a heteroaromatic system corresponding to the $(C_7–C_{19})$-aralkyl radical.

Suitable halogens (Hal) are fluorine, chlorine, bromine and iodine.

PEG means polyethylene glycol.

The description of the indicated structures contains within the scope of the invention all the possible optical antipodes.

EXAMPLES (1R, 2R)-N,N'-bis(3,5-di-tert-butylsalylicene)-1,2-cyclohexanediamino cobalt (II) (122 mg) is converted into the catalytically active species by the procedure of Jacobsen (U.S. Pat No. 5,929,232; U.S. Pat No. 5,665,890; JACS 1999, 121, 4147f.).

Activated catalyst is added to a solution of 2.33 g of the racemic epoxide of 4-pentenoic acid ethyl ester in 1 ml of dry THF. The reaction mixture is then cooled to 0° C. 165 µl of $H_2O$ are then added to the mixture in the course of a few minutes. The reaction mixture is then stirred for 2 days, during which it slowly warms to room temperature. The THF is then removed in vacuo, and 4 ml of dry TFA are added at 0° C. to the residue. After stirring for 20 minutes at 0° C., a thin-layer chromatogram (100% EtOAc, $SiO_2$) shows that conversion to (I) is complete. The reaction mixture was freed of TFA in vacuo, residues of TFA being removed by addition of toluene and subsequent evaporation. The reaction mixture is then distilled at 12 mbar, 160–200° C. sump temperature. 2.58 g of a viscous oil are obtained.

Chiral GC analysis showed: 89% S: 11% R.

What is claimed is:

1. Process for the preparation of enantiomerically enriched 4-hydroxymethyl-γ-butyrolactone (I) by kinetic racemate cleavage of racemic epoxide of the general formula (II)

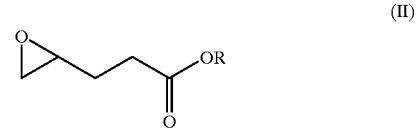

wherein R represents a $(C_1–C_8)$-alkyl radical, a $(C_8–C_{16})$-aryl radical, with a nucleophile and a catalyst that contains as the reaction center a tetradentate enantiomerically enriched metal-salene complex, and subsequent conversion to (I).

2. Process according to claim 1, wherein the catalyst contains an enantiomerically enriched complex of the general formula (III)

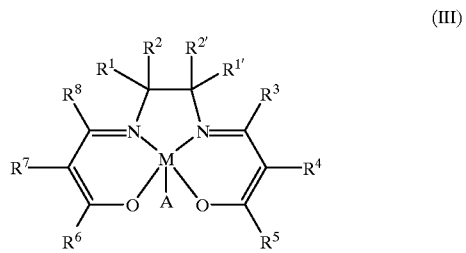

wherein
M=Cr, Co;
A represents a counter-ion or nucleophile;
$R^1$, $R^2$, $R^{1'}$, $R^{2'}$ each independently of the others represents H, $(C_1–C_8)$-alkyl, $(C_1–C_8)$-alkoxy, $(C_2–C_8)$-alkoxyalkyl, $(C_6–C_{18})$-aryl, $(C_7–C_{19})$-aralkyl, $(C_3–C_{18})$-heteroalkyl, $(C_4–C_{19})$-heteroaralkyl, $(C_1–C_8)$-alkyl-$(C_6–C_{18})$-aryl, $(C_1–C_8)$-alkyl-$(C_3–C_{18})$-heteroaryl, $(C_3–C_8)$-cycloalkyl, $(C_1–C_8)$-alkyl-$(C_3–C_8)$-cycloalkyl, $(C_3–C_8)$-cycloalkyl-$(C_1–C_8)$-alkyl;
wherein at least one of the radicals may not be H, or $R^1$ and $R^{1'}$ are bonded via a $(C_3–C_5)$-bridge that may be mono- or poly-substituted by $(C_1–C_8)$-alkyl, $(C_1–C_8)$-acyl, $(C_1–C_8)$-alkoxy, $(C_2–C_8)$-alkoxyalkyl, and/or may contain hetero atoms selected from the group consisting of N, O, P, and S;
$R^3$, $R^8$ each independently of the others represents H, $(C_1–C_8)$-alkyl, $(C_1–C_8)$-alkoxy, $(C_6–C_{18})$-aryl;
$R^4$, $R^5$, $R^6$, $R^7$ each independently of the others represents H, $(C_1–C_8)$-alkyl, $(C_1–C_8)$-alkoxy, $(C_2–C_8)$- alkoxyalkyl, $(C_{1-C8})$-acyloxy, $(C_1-C_8)$-acyl, $(C_6-C_{18})$-aryl, $(C_7-C_{19})$-aralkyl, $(C_3-C_{18})$-heteroalkyl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_3-C_8)$-alkyl-$(C_3-C_8)$-cycloalkyl, $(C_3-C_8)$-cycloalkyl-$(C_1-C_8)$-alkyl;

or $R^4$ and $R^5$ and/or $R^6$ and $R^7$ are bonded via a $(C_3-C_5)$-bridge that may contain one or more double bonds and/or may be mono- or poly-substituted by $(C_1-C_8)$-alkyl, $(C_1-C_8)$-acyl, $(C_1-C_8)$-alkoxy, $(C_2-C_8)$-alkoxyalkyl, and/or may contain hetero atoms selected from the group consisting of N, O, P, and S.

3. Process according to claim 2, wherein the complex contains an enantiomerically enriched catalyst of the general formula (IV)

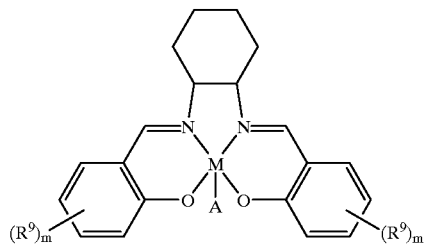

(IV)

wherein m=from 0 to 4;

M=Cr, Co;

A=Cl, $BF_4$, $SbF_6$, $(C_1-C_8)$-acyloxy, OH, $H_2O$, $OC(CF_3)_3$, $O(C_6-C_{18})$-aryl;

$R^9$=$(C_1-C_8)$-alkyl, $(C_6-C_{18})$-aryl.

4. Process according to claim 1, wherein the kinetic racemate cleavage is carried out without a solvent or in an inert organic solvent.

5. Process according to claim 1, wherein the racemate cleavage is carried out at temperatures of from −40° C. to +50° C., preferably from −20° C. to +30° C.

6. Process according to claim 1, wherein water is used as the nucleophile in the kinetic racemate cleavage.

7. Process according to claim 6, wherein the enantiomerically enriched diol of the general formula (V) obtained in the kinetic racemate cleavage with water

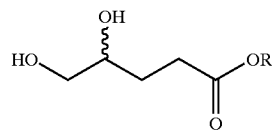

(V)

is transesterified to enantiomerically enriched 4-hydroxymethyl-γ-butyrolactone (I).

8. Process according to claim 1, wherein the enantiomerically enriched epoxide of the general formula (II) obtained in the kinetic racemate cleavage

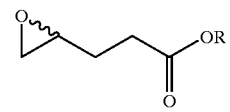

(II)

is converted with acid catalysis to enantiomerically enriched 4-hydroxymethyl-γ-butyrolactone.

9. Process according to claim 7, wherein the transesterification of the enantiomerically enriched diol (V) and the cyclisation of the enantiomerically enriched epoxide (II) care carried out together in one reaction container.

10. Method of preparing a substance having biological activity, comprising:
    adding 4-hydroxymethyl-γ-butyrolactone (I) prepared according to claim 1, to a biologically acceptable carrier.

11. Process according to claim 4, wherein said inert organic solvent is selected from the group consisting of ether, THF, and MTBE.

12. Process according to claim 4, wherein said inert organic solvent is THF or MTBE.

13. Process according to claim 8, wherein the transesterification of the enantiomerically enriched diol (V) and the cyclisation of the enantiomerically enriched epoxide (II) care carried out together in one reaction container.

14. Process according to claim 8, wherein the acid used in said acid catalysis is selected from the group consisting of TFA, $HClO_4$, $H_2SO_4$, $H_3PO_4$, and polymerically bonded acids.

* * * * *